United States Patent
Wei et al.

(10) Patent No.: US 7,387,038 B2
(45) Date of Patent: Jun. 17, 2008

(54) WIDE RANGE CONSTANT CONCENTRATION PARTICLE GENERATING SYSTEM

(75) Inventors: Qiang Wei, Novi, MI (US); Ichiro Asano, Konan (JP)

(73) Assignee: Horiba Instruments, Inc., Irvine, CA (US)

( * ) Notice: Subject to any disclaimer, the term of this patent is extended or adjusted under 35 U.S.C. 154(b) by 179 days.

(21) Appl. No.: 11/193,642

(22) Filed: Jul. 29, 2005

(65) Prior Publication Data

US 2007/0028662 A1 Feb. 8, 2007

(51) Int. Cl.
*G01N 15/02* (2006.01)

(52) U.S. Cl. .................. 73/865.5; 239/71; 73/1.05

(58) Field of Classification Search ............ 73/1.04, 73/1.05, 865.5
See application file for complete search history.

(56) References Cited

U.S. PATENT DOCUMENTS

| | | | | |
|---|---|---|---|---|
| 3,434,977 | A | * | 3/1969 | Neugebauer .................. 252/1 |
| 3,790,079 | A | * | 2/1974 | Berglund et al. ............... 239/3 |
| 3,975,953 | A | | 8/1976 | Smith et al. |
| 4,445,615 | A | | 5/1984 | Bohme et al. |
| 4,586,367 | A | | 5/1986 | Lewis |
| 4,687,929 | A | | 8/1987 | Browner et al. |
| 5,090,258 | A | | 2/1992 | Yamasaki et al. |
| 5,156,776 | A | * | 10/1992 | Loedding et al. ............ 261/27 |
| 5,609,798 | A | | 3/1997 | Liu et al. |
| 5,628,937 | A | * | 5/1997 | Oliver et al. .................. 264/9 |
| 5,756,360 | A | | 5/1998 | Harvey et al. |
| 6,200,819 | B1 | | 3/2001 | Harvey et al. |
| 6,331,290 | B1 | | 12/2001 | Morgan |
| 6,607,597 | B2 | * | 8/2003 | Sun et al. .................... 118/309 |
| 6,639,670 | B2 | | 10/2003 | Carpenter |
| 6,729,195 | B2 | | 5/2004 | Graze, Jr. |
| 6,911,649 | B2 | | 6/2005 | Hess et al. |
| 2004/0202578 | A1 | * | 10/2004 | Burtscher et al. ............. 422/83 |
| 2007/0242261 | A1 | * | 10/2007 | Liu .............................. 356/37 |

FOREIGN PATENT DOCUMENTS

JP 58083237 A * 5/1983

OTHER PUBLICATIONS

TSI, Model 3076 Constant Output Atomizer, Instruction Manual, Jun. 2005.

* cited by examiner

*Primary Examiner*—Hezron E. Williams
*Assistant Examiner*—Nashmiya S Fayyaz
(74) *Attorney, Agent, or Firm*—Brooks Kushman P.C.

(57) ABSTRACT

A particle generating system includes an aerosol generator, an ejector diluter, and an aerosol diluter. The ejector diluter receives the generated aerosol and dilutes the aerosol to an expected raw concentration. The aerosol diluter further dilutes the aerosol to a concentration in the range of 0% to 100% of the expected raw concentration. The aerosol diluter includes a mini cyclone for diluting the aerosol. The particle generating system may be configured to provide variable concentrations of monodisperse or polydisperse aerosols for instrument calibration. The system may provide constant concentrations in the range of 0% to 100% of the raw concentration. The mini cyclone makes the system compact, and the system may be portable.

13 Claims, 3 Drawing Sheets

WIDE RANGE CONSTANT CONCENTRATION PARTICLE GENERATING SYSTEM

BACKGROUND OF THE INVENTION

1. Field of the Invention

The invention relates to particle generating systems and to calibrating particle instruments.

2. Background Art

Particle instruments have been widely applied to detect particulate matter level (mass and number) in ambient air, specific environments, and combustion engines, etc. To ensure that these instruments perform accurately, frequent calibrations with different constant concentration aerosols are extremely necessary.

Currently, aerosol generators, such as atomizer and propane burner, etc., have been widely used to generate particles. Many different types of diluters have been applied to dilute particles to different concentrations as well. However, the dilution ratio range is narrow, and does not provide concentration in the range of 0% to 100%.

By combining these two techniques, calibration aerosol is available to calibrate particle instruments. Since aerosol generators and diluters are in separate units, the units must be put together correctly to generate the expected concentration aerosol. The setup procedure is time-consuming, and not efficient. Many variations may be involved during the setup. As a result, greater uncertainties may be introduced into the calibrated instrument.

SUMMARY OF THE INVENTION

It is an objective of the invention to provide an improved particle generating system.

The invention involves generating well known concentrations of mono- or polydisperse aerosol for instrument calibration. In a preferred implementation, accurate aerosol concentration is available in the range of 0% to 100% of the raw aerosol by diluting the raw aerosol.

In accordance with the invention, a wide range constant concentration particle generating system provides calibration aerosol with well known characteristics. In one aspect, the invention may involve integrating an aerosol generator, ejector diluter, and aerosol diluter into a single system.

In an exemplary approach to carrying out the invention, an ejector diluter dilutes aerosol to the expected raw concentration. An aerosol diluter dilutes the aerosol further to a concentration in the range of 0% to 100% of the raw concentration. According to the invention, a mini cyclone on the aerosol diluter is used to mix aerosol, which dilutes raw aerosol from the ejector diluter and aerosol generator. Since the cyclone results in low particle losses and the aerosol diluter provides accurate dilution ratios, accurate concentration in the expected size range and similar size distributions are obtained in the range of 0% to 100% of the raw aerosol concentration. In this particular approach, the cyclone removes large size particles as well. And so as a result, this protects calibrated instruments from malfunctions. By using the mini cyclone instead of a traditional tunnel for mixing, the actual size of the diluter may be reduced. A PID loop controls the dilution ratio as constant on the aerosol diluter when a constant dilution ratio and concentration are expected.

The aerosol generator generates polydisperse aerosol under most circumstances. By feeding the aerosol generated by the aerosol generator into a size instrument, such as a differential mobility analyzer (DMA), monodisperse aerosol with 0% to 100% of raw concentration becomes available.

BRIEF DESCRIPTION OF THE DRAWINGS

FIG. 1 depicts a flow schematic for a wide range constant concentration particle generating system that provides polydisperse aerosol for calibration in accordance with a preferred embodiment of the invention;

FIG. 2 depicts a flow schematic for a wide range constant concentration particle generating system that provides monodisperse aerosol for calibration in accordance with a preferred embodiment of the invention;

FIG. 3 illustrates an ejector diluter;

FIG. 4 illustrates an aerosol diluter; and

FIG. 5 illustrates an alternative design of the aerosol diluter.

DETAILED DESCRIPTION OF THE PREFERRED EMBODIMENTS

As shown in FIGS. 1 and 2, in the preferred embodiment, the wide range constant concentration particle generating system includes aerosol generator 10, aerosol conditioning unit 12, neutralizer 14, high efficiency particle filter (HEPA) 16, ejector diluter 18, aerosol diluter 20, and control system 22. The system also includes a suitable vacuum source, and particle-free compressed air, etc. FIGS. 1 and 2 show the flow schematic of the system for poly- and monodisperse aerosol, respectively.

In FIG. 1, aerosol generator 10 generates aerosol by atomizing a liquid solution with compressed air, or combusting propane or diesel fuel on a burner, or other means. The type of generator used is determined by the calibrated instruments and their applications. For example, if the instrument is a condensation particle counter, which measures the particle number concentration, the atomizer is a good choice for the generator.

After aerosol flows into conditioning unit 12, water or liquid drops or vapor is removed. Then, the aerosol moves into neutralizer 14. By adjusting needle valve 15, the extra flow can be vented from HEPA filter 16, where particles in aerosol are removed, if the flow required in ejector diluter 18 is less than that generated by aerosol generator 10. Under some circumstances, the flow is sucked into ejector 18 through HEPA filter 16, where particles in ambient air are removed, if generator 10 does not generate enough flow for ejector diluter 18. With an inlet open on HEPA filter 16, the flow pressure in the aerosol can be stabilized.

In neutralizer 14, the aerosol is charged to Boltzmann equilibrium. As a result, particle losses, which are caused by static charges on particles, are reduced. The aerosol is diluted in ejector diluter 18 to the expected concentration. Partial flow from ejector 18 moves into aerosol diluter 20. A large fraction of the aerosol is vented.

When the dilution ratio is 1:1 on aerosol diluter 20, the concentration of aerosol from ejector diluter 18 is measured by calibrated instrument 24. This number is recorded and saved in computer 22 as the raw concentration of the aerosol. By inputting the expected percentage concentration from the computer, the computer and PID loop in control software control the aerosol diluter 20 to the expected dilution ratios. 100% concentration means no dilution on the aerosol, and 0% concentration means no aerosol into the calibrated instrument 24.

In FIG. 2, the aerosol flowing from neutralizer 14 is connected to a differential mobility analyzer (DMA) 26 instead of directly to ejector diluter 18. DMA 26 can output single size (monodisperse) particles by running at constant voltage. The monodisperse aerosol flows into ejector diluter 18, which functions to vent or compensate the flow from DMA 26 while the aerosol from DMA 26 is higher or lower than that expected. Except for these noted differences, operation of the system for monodisperse aerosol is the same as operation of the system for polydisperse aerosol.

Figure 3:
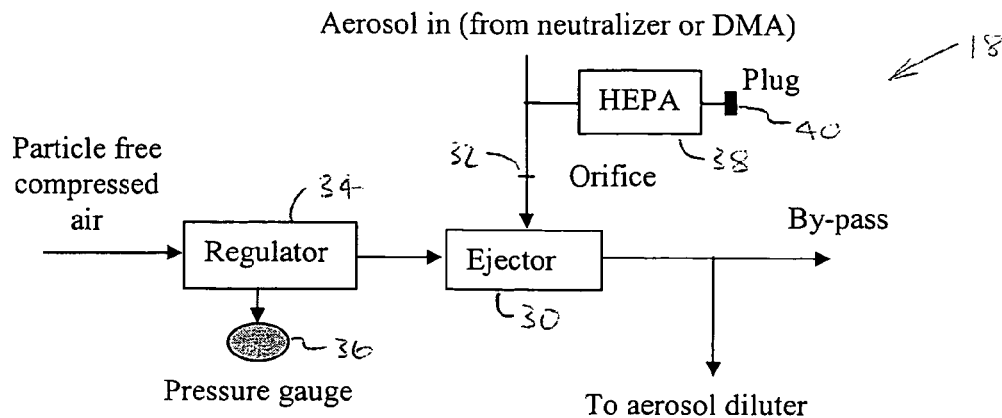

FIG. 3 illustrates the flow schematic of ejector diluter 18 in more detail. The flow schematic includes ejector 30, orifice 32, pressure regulator 34, and pressure gauge 36, HEPA filter 38, as well as the particle free compressed air and by-pass.

Ejector 30 is operated by particle free compressed air. When compressed air flows through ejector 30, vacuum is generated at the inlet side of ejector 30. The vacuum sucks the aerosol flow, which is from neutralizer 14 or DMA 26, into the ejector. Aerosol is mixed with particle free compressed air quickly and uniformly in the ejector. Most of the mixture from ejector 30 is vented, and a small fraction of the mixture flows into the aerosol diluter.

With a specific size orifice 32, different dilution ratios can be obtained by adjusting the pressure of the compressed air. Under most circumstances, the greater the compressed air pressure is, the higher the dilution ratio is. Put another way, the lower the compressed air pressure is, the lower the dilution ratio is.

The size of orifice 32 is the other major factor to adjust dilution ratio on ejector 30. With a larger size orifice, a smaller dilution ratio can be obtained. Put another way, a greater concentration of the aerosol can be obtained. With a smaller size orifice, a greater dilution ratio and lower aerosol concentration can be obtained.

Figure 1:
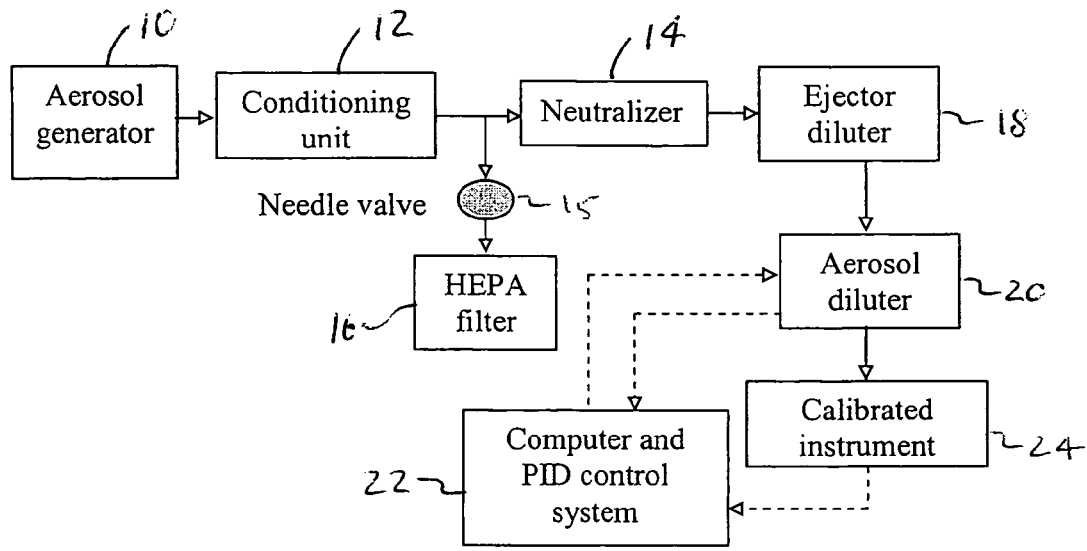

In the case where polydisperse aerosol is expected, ejector diluter 30 receives the aerosol from neutralizer 14 directly. HEPA filter 38 should be closed by plug 40, because HEPA filter 16 and needle valve 15 (FIG. 1) upstream of the neutralizer can ensure the right amount of flow into the ejector diluter by venting or sucking extra flow.

Figure 2:
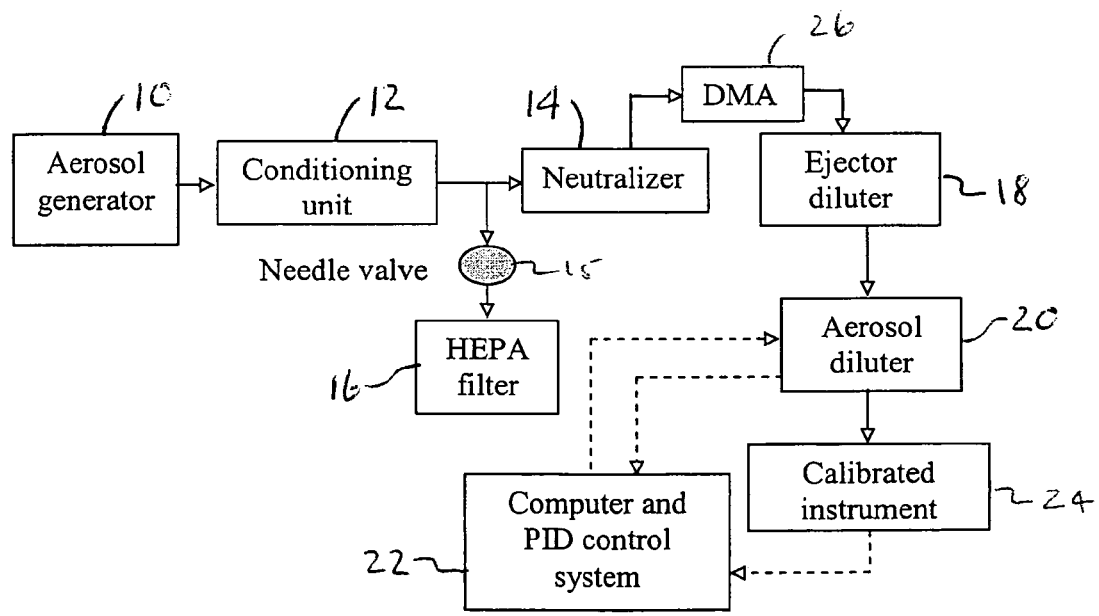

In the case where monodisperse aerosol is expected, the aerosol from neutralizer 14 moves into differential mobility analyzer (DMA) 26 (FIG. 2). DMA 26 selects single size particles by running at a fixed column voltage. A column voltage is related to a specific particle size. DMA 26 outputs constant air flow as well. This flow may be greater or less than that required by ejector diluter 18.

With continuing reference to FIG. 3, by taking off the plug 40 connected to HEPA filter 38 on the ejector diluter, the flow into the ejector diluter can be adjusted automatically. For example, when the DMA is not able to provide enough flow to the ejector diluter, ambient air filtered by the HEPA filter 38 moves into and mixes with the aerosol from the DMA; when the DMA provides more flow than that required by the ejector diluter, the extra flow from the DMA is vented through the HEPA filter 38. As a result, the adjustment of the dilution ratio on the ejector diluter does not influence the performance of the DMA.

Figure 4:
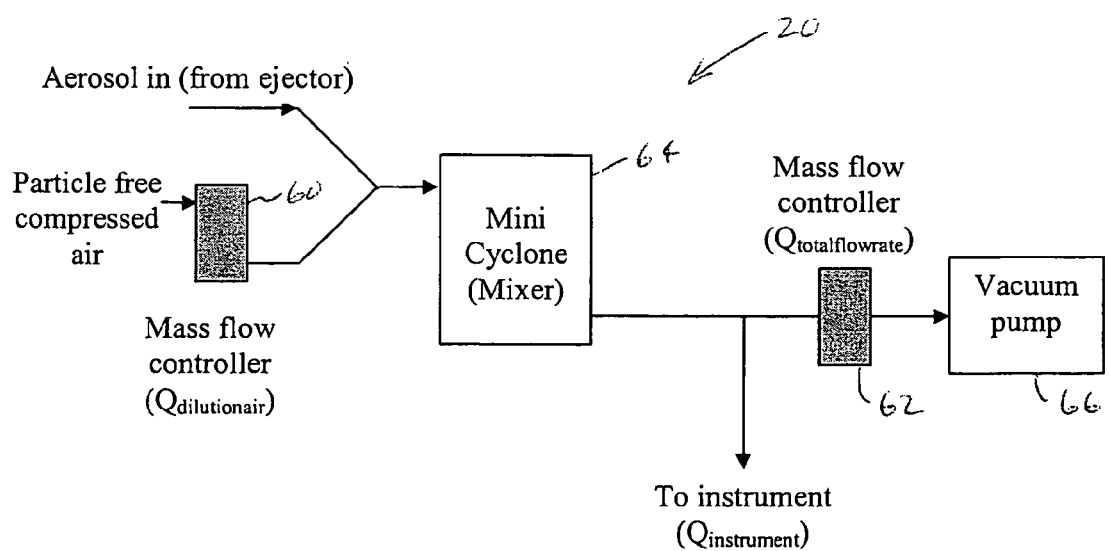

FIG. 4 illustrates the flow schematic of the aerosol diluter in more detail. This includes mass flow controller 60, mass flow controller 62, mini cyclone 64, and vacuum pump 66.

Aerosol from the ejector diluter moves into aerosol diluter 20, and uniformly mixes with particle free compressed air in mini cyclone 64. Particles larger than 2.5 micrometers are removed by cyclone 64, and cyclone 64 protects the calibrated instrument from malfunction caused by large size particles. Flow rates of the dilution air and total flow are controlled by the two mass flow controllers 60, 62. The computer software and hardware control these flow rates to obtain the expected dilution ratio or aerosol concentration. The well known flow rate of aerosol moves into the calibrated instrument 24. The extra flow is evacuated by vacuum pump 66.

The following equations show the calculation of the dilution ratio and concentration:

$$Dr = \frac{Q_{totalflowrate} + Q_{instrument}}{(Q_{totalflowrate} + Q_{instrument}) - Q_{dilutionair}}$$

$$C = \frac{C_{raw}}{Dr} = p * C_{raw}$$

$$p = \frac{1}{Dr}$$

Where, $Q_{totalflowrate}$ is total flow through the flow controller; $Q_{instrument}$ is well defined flow rate to the calibrated instrument; $Q_{dilutionair}$ is the dilution air flow rate; $C_{raw}$ is aerosol concentration from the ejector diluter; Dr is the dilution ratio on the aerosol diluter; C is expected concentration; p is the percentage concentration in 0 to 100%. All flow rates above are at standard condition or the same reference condition.

To have 100% concentration, the dilution air flow is zero. As a result, raw aerosol from the ejector only moves into the cyclone. To have 0% concentration aerosol into the calibrated instrument, $Q_{dilutionair}$ should equal to or be larger than $Q_{totalflowrate}+Q_{instrument}$ in the above equations. As a result, no aerosol flow moves into the aerosol diluter.

When the constant concentration of the aerosol is expected, the dilution ratio on the aerosol diluter needs to keep as constant. A PID loop (FIGS. 1 and 2) has been built to control the dilution ratio at the constant. By comparing the set point of the dilution ratio or the percentage concentration to the real value, the PID loop adjusts the flow rate of the dilution air. As a result, constant dilution ratio is maintained.

Figure 5:
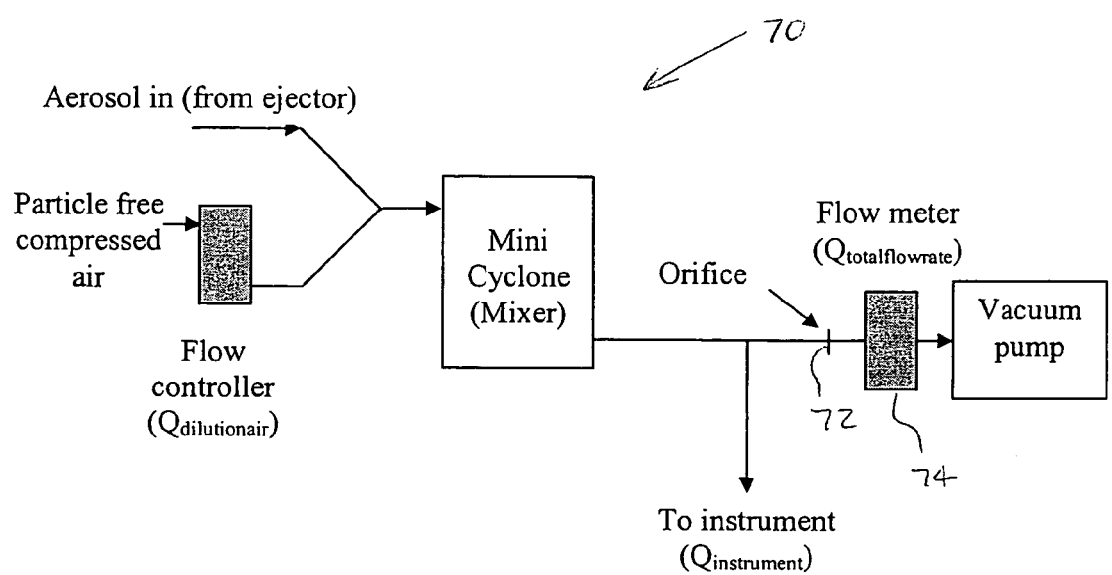

FIG. 5 shows the alternative design of the aerosol diluter at 70. The critical orifice 72 and a mass flow meter 74 replace the mass flow controller 62 shown in FIG. 4. This provides the same function as the mass flow controller for the total flow control. By changing the size of the critical orifice 72, different total flows can be obtained.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A particle generating system comprising:
   an aerosol generator for generating aerosol;
   an ejector diluter, including an ejector having an inlet side, receiving the aerosol and diluting the aerosol with a fluid to an expected raw concentration, wherein a vacuum is generated at the inlet side of the ejector when the fluid flows through the ejector to draw the aerosol into the ejector; and
   an aerosol diluter receiving the diluted aerosol and further diluting the aerosol with another fluid to a concentration in the range of 0% to 100% of the expected raw concentration, wherein the aerosol diluter includes a mini cyclone for diluting the aerosol.

2. The system of claim 1 further comprising:
a conditioning unit between the aerosol generator and the ejector diluter, the conditioning unit removing vapor from the generated aerosol.

3. The system of claim 1 further comprising:
a neutralizer between the aerosol generator and the ejector diluter, the neutralizer charging the aerosol to Boltzmann equilibrium.

4. The system of claim 1 further comprising:
a high efficiency particulate filter accommodating flow between ambient and the ejector diluter such that flow from the aerosol generator can be vented from the filter or flow can be drawn through the filter to the ejector diluter, depending on the required flow of the ejector diluter.

5. The system of claim 1 further comprising:
a PID loop controlling a dilution ratio for the aerosol diluter.

6. The system of claim 5 wherein the PID loop controls the dilution ratio as constant.

7. The system of claim 1 further comprising:
a size instrument receiving the generated aerosol from the aerosol generator and producing a monodisperse aerosol for reception by the ejector diluter.

8. The system of claim 7 wherein the size instrument is a differential mobility analyzer.

9. The system of claim 1 wherein the aerosol generator generates polydisperse aerosol that is received by the ejector diluter.

10. The system of claim 1 wherein the aerosol diluter further comprises:
a first mass flow controller connecting a particle-free source to the mini cyclone for diluting the aerosol;
a vacuum pump;
a second mass flow controller connecting the mini cyclone to the vacuum pump;
and
an outlet between the second mass flow controller and the mini cyclone for connecting to an instrument.

11. The system of claim 1 wherein the aerosol diluter further comprises:
a first mass flow controller connecting a particle-free source to the mini cyclone for diluting the aerosol;
a vacuum pump;
a mass flow meter and critical orifice between the mini cyclone and the vacuum pump; and
an outlet between the second mass flow controller and the mini cyclone for connecting to an instrument.

12. The system of claim 1 wherein the fluid comprises particle free compressed air.

13. The system of claim 1 wherein the another fluid comprises particle free compressed air.

* * * * *